US00PP23551P3

(12) United States Plant Patent
Meilland

(10) Patent No.: US PP23,551 P3
(45) Date of Patent: Apr. 23, 2013

(54) GRANDIFLORA ROSE PLANT NAMED 'MEIKANARO'

(50) Latin Name: *Rosa hybrida*
Varietal Denomination: Meikanaro

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/067,926

(22) Filed: Jul. 7, 2011

(65) Prior Publication Data

US 2013/0014298 P1 Jan. 10, 2013

(51) Int. Cl.
*A01H 5/00* (2006.01)

(52) U.S. Cl. ..... Plt./134

(58) Field of Classification Search ..... Plt./134, Plt./133, 132
See application file for complete search history.

*Primary Examiner* — Kent L Bell

(74) *Attorney, Agent, or Firm* — Buchanan Ingersoll & Rooney

(57) ABSTRACT

A new and distinct variety of Grandiflora rose plant is provided that abundantly and substantially continuously forms attractive double blossoms that are yellow finishing to cream yellow in coloration. The vegetation is vigorous and a bushy growth habit is displayed. Attractive conical buds are formed, and the disease resistance is good. The plant is particularly well suited for providing distinctive attractive ornamentation in the landscape.

1 Drawing Sheet

Botanical/commercial classification: *Rosa hybrida*/Grandiflora Rose Plant.

Varietal denomination: cv. Meikanaro.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the product of the cross of the 'Bucbi' variety (U.S. Plant Pat. No. 4,225) and the 'Meipsilon' variety (non-patented in the United States). The male parent (i.e., the pollen parent) was the 'Meironsee' variety (U.S. Plant Pat. No. 8,496).

The parentage of the new variety can be summarized as follows:

('Bucbi'×'Meipsilon')×'Meironsee'.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms vigorous vegetation,
(b) forms a bushy growth habit,
(c) forms nicely shaped conical buds,
(d) abundantly and substantially continuously forms attractive double blossoms that are yellow finishing to cream yellow in coloration,
(e) displays attractive dense glossy dark green foliage,
(f) displays good disease resistance, and
(g) is particularly well suited for providing distinctive attractive ornamentation in the landscape.

The yellow blossom coloration contrasts nicely with the glossy dark green foliage.

The new variety well meets the needs of the horticultural industry and can be grown to advantage in parks and gardens.

The new variety can be readily distinguished from its ancestors upon an inspection of the blossoms. The female parent is non-patented, unnamed, and has not been released to the public. Unlike the new variety, the female parent is a Hybrid Tea rose and displays pale pink blossoms with soft petals. For instance, the 'Bucbi' variety forms large pink blossoms. The 'Meipsilon' variety forms bicolored red and yellow blossoms. The 'Meironsee' vareity forms orange blossoms.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meikanaro'. During test evaluation, the new variety has been named an All-America Rose Selections (AARS) winner for 2012.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during October while budded on *Rosa laxa* understock and growing outdoors at Le Cannet des Maures, Var, France.

DETAILED DESCRIPTION

Figures 1, 2, 3, 4, 5, 6, 7, 8, 9, 10, 11, 12, 13, 14, 15, 16, 17:
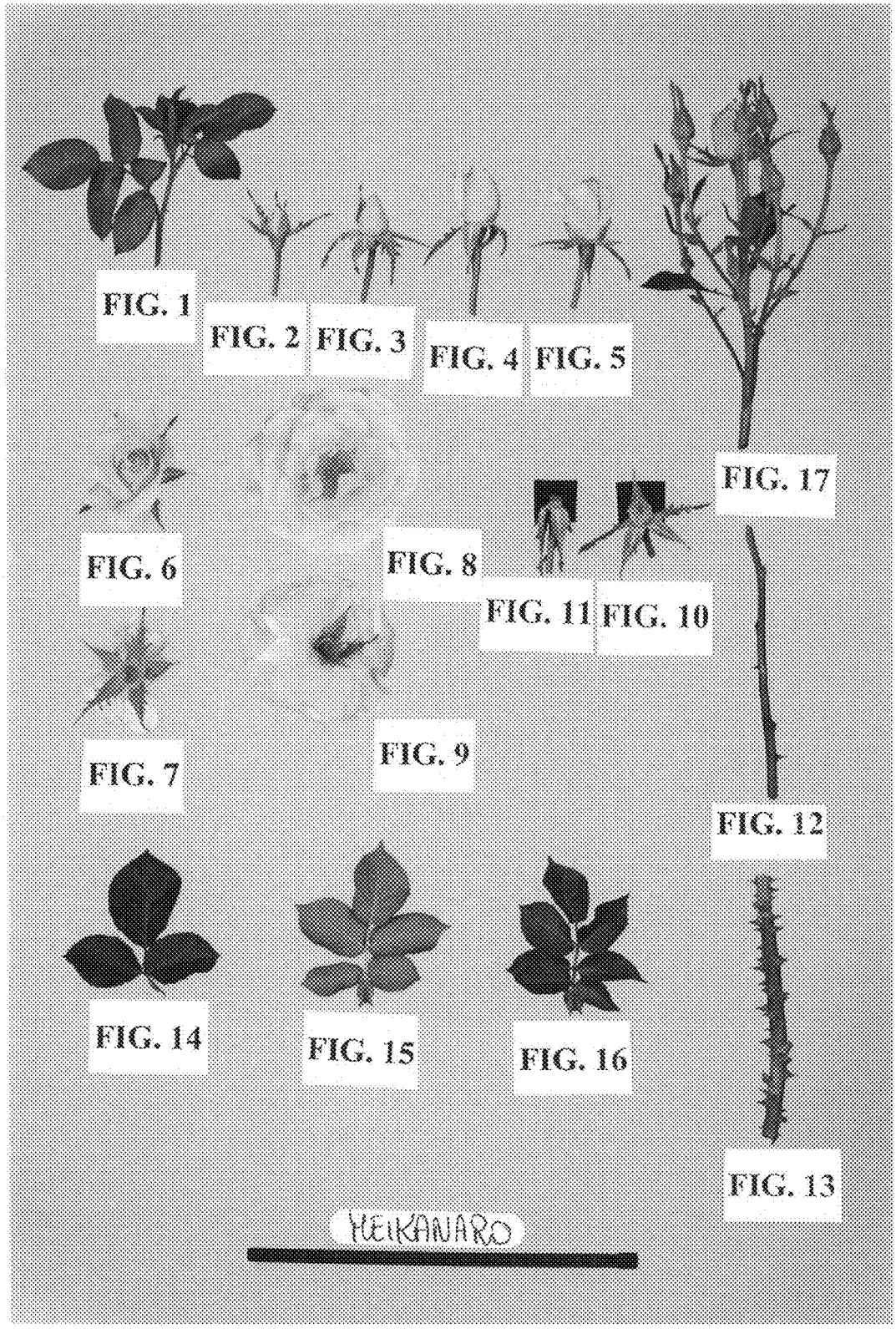
FIG. 1 illustrates a specimen of a young shoot.
FIG. 2 illustrates a specimen of a floral bud at the beginning of the opening of the sepals.
FIG. 3 illustrates a specimen of a floral bud at the further opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a flowering stem.
FIG. 13 illustrates a specimen of a main branch.
FIG. 14 illustrates a specimen of a leaf with 3 leaflets—plan view—upper surface.
FIG. 15 illustrates a specimen of a leaf with 5 leaflets—plan view—under surface.
FIG. 16 illustrates a specimen of a leaf with 7 leaflets—plan view—upper surface.
FIG. 17 illustrates a specimen of a cluster of buds.

The chart used in the identification of the colors is that of The Royal Horticultural Society (R.H.S. Colour Chart) except where ordinary color terms are utilized. Such common color terms are to be accorded their customary dictionary significance. The description is based upon the observation of plants of the new variety at an age of approximately two years during the month of October while being grown at Le Cannet des Maures, Var, France.

Class: Grandiflora.

Plant:

*Growth habit*.—Bushy.

*Height*.—Commonly approximately 5.5 feet at an age of two years.

*Width*.—Commonly approximately 4.5 feet at an age of two years.

Branches:

*Color*.—Young stems: commonly near Green Group 143A. Adult wood: commonly near Green Group 138A. Texture: smooth on young stems and on adult wood.

*Thorns*.—Configuration: rather upright and elongated, slightly concave on the upper surface, short and rounded on the under surface, and with short and oval bases. Quantity and size on young stems: commonly approximately 5 on average having lengths of approximately 0.7 cm over a stem length of 10 cm, and commonly bear no small prickles. Quantity and size on adult stems: commonly approximately 10 on average having lengths of approximately 0.8 cm on average over a stem length of 10 cm, and commonly approximately 4 on average over a stem length of 10 cm having lengths of approximately 0.4 cm. Color: on young stems near Yellow-Green Group 144B, and on adult stems longer thorns commonly are near Greyed-Orange Group 166C and shorter thorns commonly are near Greyed-Orange Group 165C.

Leaves:

*Size*.—A seven-leaflet leaf commonly is approximately 6.5 cm in length on average and approximately 4 cm in width on average.

*Overall appearance*.—Very dense dark green glossy foliage.

*Leaflets*.—Shape: generally oval. Number: 3, 5 and 7 (most often). Apex: acuminate. Base: rounded. Size: the terminal leaflets commonly are approximately 6.5 cm in length on average and approximately 4 cm in width on average. Serration: slightly denticulate, small and single. Texture: firm, smooth on upper and under surfaces, and glossy on the upper surface. Color (young foliage): near Green Group 137A on the upper surface, and near Yellow-Green Group 146B on the under surface. Color (adult foliage): near Green Group 135A on the upper surface, and near Green Group 137C on the under surface.

*Petiole length*.—Commonly approximately 2.8 cm on average. Diameter: commonly approximately 2 mm on average. Texture: slightly glandular on the upper surface and commonly without prickles on the under surface. Color: near Green Group 143A on the upper surface, and near Yellow-Green Group 144B on the under surface.

*Rachis*.—Color: near Yellow-Green Group 146A on the upper surface and near Green Group 143C on the under surface.

*Stipules*.—General appearance: adnate, pectinate, and relatively broad. Size: commonly approximately 1.6 cm in length on average, and approximately 0.8 cm in width on average. Color: near Green Group 143A on the upper surface, and near Green Group 141B and Green Group 141C on the under surface.

Inflorescence:

*Number of flowers*.—Commonly approximately 1 to 3 double blossoms per stem.

*Peduncle*.—Somewhat glandular, commonly approximately 5 to 7 cm in length on average, approximately 3 mm in diameter on average, and near Yellow-Green Group 144A in coloration.

*Sepals*.—Shape: longish pointed, very pointed apex, and somewhat broad and upright at the base. Margins: with extensions and smooth between extensions. Texture: tomentose on both surfaces. Size: approximately 4.7 cm in length on average, and approximately 1.2 cm in width on average at the base. Color: near Green Group 137C on the upper surface, and near Green Group 143B on the under surface.

*Buds*.—Shape: generally conical and medium-sized. Length: approximately 1.5 cm on average. Width: approximately 1 cm at the widest point on average. Color: as the calyx breaks, near Yellow Group 3A on the upper surface and near Yellow Group 3C on the under surface.

*Flower*.—Diameter: approximately 9 to 10 cm on average. Height: commonly approximately 4.5 cm on average. Shape: cup-shaped. Color (in course of opening): upper side: near Yellow Group 10A. under side: near Yellow Group 11B. Color (when open): upper side: near Yellow Group 11B. under side: nearly Yellow Group 12C. color stability: petals lighten somewhat with maturity. Fragrance: not noticeable. Petal number: commonly approximately 33 to 35 on average under normal growing conditions. Petal shape: generally rounded, with a rounded tip and a somewhat rounded base. Petal margins: commonly reflexed. Petal texture: smooth on upper surface. Petal arrangement: imbricated and commonly without petaloids. Petal length: commonly approximately 4.3 cm on average. Petal width: commonly approximately 5 cm on average. Petal drop: good with the petals commonly detaching cleanly before drying. Stamen number: commonly approximately 153 on average. Anthers: regularly arranged around the styles, commonly approximately 3 mm in length on average, approximately 1 mm in width on average, and near Yellow Group 13A in coloration. Filaments: commonly approximately 0.6 cm in length on average, and near Yellow Group 9A in coloration. Pollen: commonly present in a moderate quantity and near Yellow Group 13A in coloration. Pistils: commonly approximately 139 on average. Styles: commonly approximately 0.7 cm in length on average, and near Yellow Group 2D in coloration. Stigmas: commonly approximately 2 mm in length, approximately 1 mm in diameter, and near Red Group 42A in coloration. Receptacle: pitcher-shaped, commonly approximately 0.8 cm in length on average, commonly approximately 0.8 cm in width at the widest point, smooth in texture, and near Green Group 143B in coloration. Hips: generally round in shape, commonly approximately 3 mm in diameter, smooth in texture, and near Yellow-Orange Group 23C in coloration.

Development:

*Vegetation*.—Very strong.

*Blooming*.—Early season, abundant and substantially continuous.

*Tolerance to diseases*.—Very good during observations to date.

I claim:

1. A new and distinct Grandiflora rose plant characterized by the following characteristics:

(a) forms vigorous vegetation, (b) forms a bushy growth habit, (c) forms nicely shaped conical buds, (d) abundantly and substantially continuously forms attractive double blossoms that are yellow finishing to cream yellow in coloration, (e) displays attractive dense glossy dark green foliage, (f) displays good disease resistance, and (g) is particularly well suited for providing distinctive attractive ornamentation in the landscape;

substantially as shown and described.

* * * * *

YEIKANARO